United States Patent [19]

Granov et al.

[11] Patent Number: 5,108,359

[45] Date of Patent: Apr. 28, 1992

[54] HEMANGIOMA TREATMENT METHOD

[75] Inventors: anatoly M. Granov; Vladimir Y. Derkach; Vladimir N. Polysalov, all of Leningrad, U.S.S.R.

[73] Assignee: Ferrotherm International, Inc., Denver, Colo.

[21] Appl. No.: 628,089

[22] Filed: Dec. 17, 1990

[51] Int. Cl.$^5$ .............................................. A61N 2/00
[52] U.S. Cl. .......................................... 600/9; 600/12; 128/804; 128/898
[58] Field of Search ............................. 606/27, 32, 33; 128/804, 399, 898; 600/9-13

[56] References Cited

U.S. PATENT DOCUMENTS

| | | | |
|---|---|---|---|
| 4,323,056 | 4/1982 | Borrelli et al. | 600/10 |
| 4,545,368 | 10/1985 | Rand et al. | 128/804 |
| 4,574,782 | 3/1986 | Borrelli et al. | 600/10 |
| 4,622,952 | 11/1986 | Gordon | 600/10 |
| 4,735,796 | 4/1988 | Gordon | 424/9 |
| 4,983,159 | 1/1991 | Rand | 600/9 |

*Primary Examiner*—Stephen C. Pellegrino
*Assistant Examiner*—Steven J. Shumaker
*Attorney, Agent, or Firm*—Phillips V. Bradford

[57] ABSTRACT

The subject of this invention is in the field of medicine, particularly surgery, and is intended for the treatment of benign tumors and angiomas. A hemangioma is an angioma, or tumor, formed by an anomalous proliferation of vascular endothelium, forming an undesirable mass, which can occur anywhere in the body. The resulting disease is known as hemangiomatosis. The method of this invention is comprised of a reduction of the arterial blood flow to the hemangioma which limits the blood circulation in the tumor mass, thus creating favorable conditions for subsequent ferromagnetic embolization from externally and selectively applied electromagnetic or ultrasound energy and sclerotization of the tumor tissue, preventing the spread of ferromagnetic particles through the vessels and into other organs and systems. At the same time, maintaining the blood flow, though reduced, prevents the development of a total necrosis due to acute impairment of the tumor's blood circulation, which significantly reduces the general toxic effect. The reduced blood stream still leaves the possibility of introducing medication into the tumor, which reduces the possibility of complications during the postembolization period.

6 Claims, No Drawings

HEMANGIOMA TREATMENT METHOD

BACKGROUND OF THE INVENTION

The subject of this invention is in the field of medicine, particularly surgery, and is intended for the treatment of benign tumors and angiomas. An hemangioma is an angioma, or tumor, formed by an anomalous proliferation of vascular endothelium, forming an undesirable mass, which can occur anywhere in the body. The resulting disease is known as hemangiomatosis.

At the present time the main methods of hemangioma treatment include surgical management, radiation therapy, physical influence from the effects of electromagnetic waves (in ranges including low, high, ultrahigh, and super high frequencies), cryotherapy or hyperthermia, and chemical treatment consisting of sclerotherapy using irritating agents.

Sclerotherapy as a method of tumor treatment is used mainly for external angiomas, located on the extremities of the body (head, neck, face, lips) and includes the introduction into angioma's lacunae of such chemical agents as 60 percent glucose solution, 76-96 percent ethyl alcohol, 1-3 percent sotradecol, and sclerovein. Reference 1, listed on page 13 of this specification provides a more detailed description of sclerotherapy.

For hemangiomatosis of internal organs the use of sclerotherapy is excluded, mainly because of the danger of the sclerosants getting into the organs and other systems through blood vessels associated with the blood circulation peculiarities of the hemangioma, and also because of the difficulties in reaching the tumors.

It is well known, in case of hemangiomatosis, the liver is most often affected. According to several different authors, 9 to 20 percent of patients who were surgically operated on for liver neoplasms had cavernous hemangiomas. These data are reported in references 2 and 3, listed on page 13 of this specification. For 59 patients with liver nodes, 20 (34 percent) of them who had received treatment at the Vyshnevsky Institute of Surgery, had hemangioma. This is reported in reference 4, listed on page 13 of this specification. A list of similar examples could be continued. It is clear that hemangiomatosis of internal organs is a rather wide-spread disease. In almost 50 percent of the cases, treatment is needed in spite of its benign nature and lack of clinical symptoms.

It should be also noted that the practice of surgical removal of hemangiomas is not yet fully accepted. Some authors consider that only easily removable hemangiomas should be repected, supposing that the risk of an operation in other cases is greater than the risk of a rupture or hemorrhage. See references 5 and 6, listed on page 14 of this specification. It is known, for example, that in 5 percent of cases treated by surgery, a spontaneous rupture of hemangiomas is experienced. Such a rupture leads to a lethal outcome in 60 to 80 percent of cases in which it occurs. This is reported in reference 7, listed on page 14 of this specification. Also, it is known that among surgical treatments for hemangiomas of internal organs, 3 to 11 percent are lethal, and general surgical complications occur i 25 to 50 percent of the cases. This is shown in reference 8, listed on page 14 of this specification. Nevertheless, at the present time, surgical treatment of hemangiomatosis of parenchmal organs is preferred over other treatments. Surgical treatment consists of either removing the organ, or a part of it together with the tumor, or in ligation or embolization of the main tumor-feeding blood vessels. In cases of a widely affected organ, an inconvenient location for surgery (for example, near main blood vessels), or a multiple nodular form of hemangiomatosis, surgical removal is impractical. The alterative in such cases is an X-ray endovascular occlusion or a ligation of the blood feeding vessels.

A known method of liver hemangioma treatment, by the ligation of the liver artery, is used in cases of unremovable tumors. This method is described in reference 9, listed on page 14 scale, however, because of lethal liver necrosis, which, according to some authors, develops in 19 percent of observed cases. This is reported in reference 10, listed on page 14 of this specification. Besides, this method requires a surgical operation, which is not always possible on patients with severe somatic disorders.

Another method, closest to the method of this invention, is the method of liver hemangioma treatment, consisting of X-ray endovascular occlusion of the liver artery. In comparison with the above mentioned, this method is less traumatic, for it does not involve a surgical operation. It is recommended for unremobalve tumors, or in cases where the patient's general grave condition presents high surgical risks. This method also has some drawbacks: embolization substance can get into other blood vessels connected with vital organs; suppurative septic complications can often develop (see reference 11, listed on page 14 of this specification); uncontrollable widely spread necrosis of the tumor, caused by acute ischemia of the organ, including the tumor, can result from momentary absolute stopping of blood flow. The result is the development of severe intoxication and insufficiency of the liver and kidney. The listed drawbacks limit the use of X-ray endovascular occlusion for treating hemangiomas. See reference 12, listed on page 14 of this specification.

SUMMARY OF THE INVENTION

The principle object, or aim, of the present invention is to broaden the possibilities for the treatment of internal hemangiomas.

According to the present invention, this aim is achieved by means of reducing the hemangioma's arterial blood flow, after which a hard ferromagnetic substance is introduced into its tissue under visual control in a local magnetic field, until it fills not more than 30 percent of the hemangioma's volume, and the hemangioma is influenced by an electromagnetic field of UHF frequencies defined as the standard frequency range from 300 to 3,000 MHz or by ultrasound energy for a period of not less than 10 minutes.

Another object, or aim, of the present invention in reducing the arterial blood flow into the hemangioma so as to limit the blood circulation in the hemangioma mass. This creates favorable conditions for the subsequent ferromagnetic embolization and sclerotization of the hemangioma tissue, preventing the spread of ferromagnetic particles through the vessels and into other organs and systems.

Yet another object, or aim, of the present invention is to influence the hemangioma tissue selectively without damaging the healthy areas of the affected organ.

Still another object, or aim, of the present invention is to provide a treatment method that allows the possibility of repeated hyperthermal treatment over along period of time without additional surgical manipulation.

DETAILED DESCRIPTION OF THE INVENTION

The invention disclosed herein is a method of hemangioma treatment comprised of a means of reducing blood flow to the hemangioma, after which a hard ferromagnetic substance is introduced into the hemangioma tissue under visual control in a local magnetic field until it fills not more than 30% of the hemangioma's volume, after which it is influenced by an electromagnetic field of UHF frequencies or ultrasound energy for 10 minutes or more.

In one embodiment of the present invention, it is advisable to use hexaferrite of barium as the hard ferromagnetic substance in the form of a suspension in the 0.9 percent solution of sodium chloride, the proportion of the solid and liquid phase being from 1:5 to 1:10. The total volume of the substance should not exceed 30 percent of the hemangioma's size.

One treatment of the hemangioma with electromagnetic field in the range of super high and ultrasonic frequencies could be done. If during the control test there are found functioning hemangioma areas, the treatment should be repeated.

The reduction of the arterial blood flow limits the blood circulation in the hemangioma mass, thus creating favorable conditions for the subsequent ferromagnetic embolization and sclerotization of the hemangioma tissue, preventing the spread of ferromagnetic particles through the vessels and into other organs and systems. At the same time, maintaining the blood flow, though reduced, prevents the development of a total necrosis due to acute impairment of the hemangioma's blood circulation, which significantly reduces the general toxic effect. Besides, the reduced blood stream still leaves the possibility of introducing medication into the hemangioma, which reduces the possibility of complications during the postembolization period.

Using the ferromagnetic suspension in aqueous solution and a local magnetic field in the hemangioma's zone provides for reliable hemangioma embolization due to creating a compact magnetic system in it, excluding its desegregation and dissipation of he ferromagnetic particles through blood vessels into other organs and systems. The created compact magnetic system, having porous structure, strongly slows down the blood flow in the hemangioma's vascular lacunae, after which the blood cells precipitate within its network (accumulate in its cell-structures) with the development of a mixed thrombus, that is intensified by magnetic features of the system itself, as well as by the subsequent hyperemic effect due to the use of electromagnetic fields of the super high and ultrasonic frequencies. Afterwards the occluded hemangioma's tissues are replaced by fibroid tissue.

Visual control over the introduction of the medication, including direct observation of the place of introduction, as well as the possible ultrasonic or X-ray examination, provides for the introduction of the hard ferromagnetic substance into the hemangioma without its getting into adjacent areas of the organ. This makes it possible to influence the hemangioma's tissue selectively without damaging the healthy areas of the organ.

As it was determined during clinical observations, filling the hemangioma with hard ferromagnetic substance not exceeding 30 percent of its volume, helps to prevent a wide necrosis of the hemangioma could otherwise lead to the above mentioned complications.

Influencing the hemangioma with electromagnetic field of UHF and ultrasonic frequencies warms up the hemangioma area, while its compact magnetic system reduces the hemangioma's heat emission because of a reduction in local blood flow.

It was shown in our experiments with animals, that the intravascular introduction of the hard ferromagnetic substance in the local magnetic field, achieved the effect of the thrombus development under the influence of electromagnetic fields of UHF or ultrasonic frequencies in 10 minutes or more. This was confirmed by clinical observations during hemangioma treatment. The presence of a stable compact magnetic system in the hemangioma's area where the hemangioma tissue remains, which could be found out by control examinations, makes repeated local hyperthermia possible. Thus, according to the present invention, a new method results in the thrombosis of the hemangioma with its subsequent replacement by fibroid tissue, without the development of the hemangiomas necrosis, without a grave intoxication, and without the dissipation of the embolization substance. In addition, the method of this invention provides the simultaneous thrombo-embolizing influence on the arterial as well as the venous hemangioma's components, and also the possibility of repeated hyperthermal treatment after a long period of time without additional surgical manipulation. The present invention thus broadens the possibilities of using the suggested method of hemangioma treatment, even in those cases when other methods entail a high risk for the patient.

ENABLEMENTS OF THE INVENTION

A practical enablement of the present invention consists of the following method: A selective catheterization of the hemangioma's supplying artery is done on a patient with a cavernous hemangioma under general or local anesthesia. Through the catheter, under X-ray control, a metal spiral of the Gianturko type is introduced into the artery until the blood flow is reduced. Then, under visual (ultrasonic or X-ray, for example) control, the hemangioma is punctured, and the suspension of the hard ferromagnetic substance is introduced into it. In the 0.9 percent solution of sodium chloride, the proportion of the solid and liquid phases being from 1:5 to 1:10, until it fills not more than one third of the hemangioma's volume, the source of the local magnetic field being simultaneously located over the hemangioma. After the elimination of the external magnetic field, the hemangioma is subjected to electromagnetic fields of the UHF or ultrasonic frequencies not less than 10 minutes. If necessary, antibacterial and anesthetic medication is introduced through the catheter during the following 3-4 days. The achieved medical effect is estimated not earlier than after 2 months, and if the tumor tissue remains, hyperthermic treatment is repeated.

EXAMPLE 1

Patient N, born 1943, medical history No. 10, was admitted to the clinic on Jan. 2, 1989. Diagnosis: Cavernous hemangioma of the right lobe of the liver, segments 6, 7, 8 affected.

She was disturbed by permanent subcostal pain on the right with irradiation to the right lumbral area of her back. She considered herself sick for a year. She has suffered from scoliosis since early childhood.

The ultrasonic examination of the liver confirmed a cavernous hemangioma 15 cm in diameter in the right lobe. The scintigraphic examination proved the size of the organ to be 20-14-12-17 cm, regularly located, and round in form. A focal hypofixation of the radiofarm-preparation 10 cm in size could be determined in the rear projection of segments 7 and 8. The clinical blood tests showed transitory thrombocitopenia. Biochemical reports of the functional liver condition seemed normal.

A celiacography determined the more precise localization of the cavernous hemangioma of the liver's right lobe and its relation to the blood vessels (segments 6, 7, and 8 of the liver were affected. Due to the large size of the tumor and pronounced scoliosis, which excluded the possibility of a radical operation for the tumor's removal, it was decided to make an intravascular intrusion. The arterial blood flow reduction was made by the introduction through a catheter of a metal spiral of Giantuko type into the right lever artery supplying the hemangioma. After the procedure, the catheter was removed. After 2 hours the patient noted moderate pain in the liver area, weakness, and nausea. The palpitation determined small local pain under the ribs on the right. The above mentioned clinical symptoms regressed during the following 5 days.

For the purpose of influencing the venous component of the hemangioma's blood flow, it was decided to make a local ferromagnetic embolization of the tumor by means of a puncture through the skin and through the liver under echographic control. Taking into account the hemangioma's volume (1687 cm$^3$), the chosen amount of the preparation in the 0.9 percent solution of sodium chloride, the proportion of the solid and liquid phases being 1:5 was 200 cm$^3$ (12 percent of the tumor's volume). Under local novocaine anesthesia a skin-penetrating liver-penetrating targeted puncture of the hemangioma of the right lobe of the liver was made under echographic control with the introduction of the mentioned preparation. At the same time, a permanent magnetic field was applied over the liver, the field strength in the place of the preparation introduction being 0.6 Tesla. The external source of the permanent magnetic field was held for 10 minutes.

During the treatment and for the following 6 days the patient noticed the aggravation of the pain in the liver area. The clinical biochemical reports, including the serum iron, remained at the previous levels. During the mentioned period of time the patient received analgesics and antibiotics. On Feb. 16, 1989, in 2 and ½ weeks after the ferromagnetic embolization the patient was discharged from the hospital in satisfactory condition. During the control X-ray examination the ferromagnetic preparation in the tumor was compact and stable. After 2 or 3 weeks, an ultrasonic examination of the hemangioma showed thrombosis and partial necrosis of the tumor in about 70 percent of its volume. The remaining intact zone of the tumor was 30 percent. To increase the medical effect, the patient was treated 28 days after the procedure with the local hyperthermia of the tumor area was electromagnetic radiation of UHF frequencies. The radiation power was 15 watts. The duration of the procedure was 25 minutes. During the treatment the patient's condition remained satisfactory. There were no complaints. Hemodynamic indications remained the same. After 3 months, the control echographic examination showed that the tumor reduced in half. It became 8 cm in diameter, and her whole volume was replaced by fibroid tissue. The patient feels well. She has no complaints.

EXAMPLE 2

Patient P., born 1923, medical history No. 2052, was admitted to the clinic with the diagnosis: A tumor of the liver's right lobe. From time to time had a feeling of heaviness under the ribs on the right. During a physical examination 2 months before he was admitted to the hospital, a liver enlargement was detected. An echography and a computer tomography of the liver showed a tumor of the right lobe. For a long time the patient suffers from hypertonic disease and from diabetes.

On the patient's admission to the Institute's clinic, an ultrasonic examination conformed the existence of a tumor with uneven outline in the right lobe of the liver (segments 5, 6, 7, and 8) 12×13 cm in size. The clinical blood tests showed transitory thrombopenia (from $112 \times 10^9/1$ to $254 \times 10^9/1$). Under local anesthesia by novocaine solution, for diagnostic purposes, a skin-penetrating, penetrating, liver penetrating punctural biopsy of the tumor was made under echographic control. A morphological analysis of the bioptic tissue showed symptoms of a cavernous tumor. Coagulogramma, as well as the biochemical reports of the liver's functional condition, including the level of the serum glucose, were according to the patient's age. In 2 weeks after his admission, an angiography was done, which conformed a cavernous tumor in the right lobe of the liver (segments 5, 6, 7, and 8) and its relation to the main blood vessels of the organ. Due to the large affected volume, its close location to the main blood vessels and the high risk of a liver resection, it was decided to perform the intravascular intrusion. Through a catheter in the liver's proper artery, a metal spiral of the Giantuko type was introduced into the vessel until the reduction of the arterial blood flood was achieved. Its level was controlled by X-rays using contrast substance. During the treatment, and for the following 4 days the patient had moderate dull pain in the liver area, a short temperature increase to 37.4° C. for 2 days. A local painless under the ribs on the right could be determined. The patient received antibacterial therapy and analgetics. The clinical blood tests showed an increased level of leukocytes up to $11 \times 10^9/1$ and erythrocyte precipitation up to 40 mm/h, which went down to its previous level after 5 days. Biochemical indications of the liver's functional condition did not differ from normal, except GGTP (32.4 mm/ts) and fibrinogen (11.5 g/l) since the day of his treatment until his discharge from the hospital.

Twelve days after the intravascular intrusion under local anesthesia, with additional neuroleptanalgesia and under echographic control, a skin-penetrating, liver-penetrating targeted puncture of the hemangioma was down with subsequent local ferromagnetic embolization. The local ferromagnetic embolization was done by means of introducing into the tumor mass, 863 cm$^3$ volume of the calculated amount of the preparation in the 0.9 percent sodium chloride solution. The total volume was 84 cm$^3$, that is 10 percent of the tumor's volume. The proportion of the solid and liquid phases was 1:5. At the same time, a permanent magnetic field was created over the liver, its tension being 0.6 Tesla at the place where the preparation was introduced. The external source of the magnetic field was held over the liver for 10 minutes. During the treatment and for the following 4 days the pain in the liver area increased.

Clinical biochemical reports, including the iron in serum level, remained normal. During the period the patient received antibiotics and analgetics. In 18 days after the ferromagnetic embolization the patient was treated with the local hyperthermia, the tumor area was influenced by electromagnetic radiation of UHF frequencies. Its radiation power was 25 watts and its duration was 5 minutes. During the treatment and over the following days the patient stayed in good condition and had no complains. His blood pressure remained increased at the level of 160/90. The biochemical reports of his liver's functional condition showed an increase of the GGPT up to 23.1 mm and of the fibrinogen up to 6.7 g/l. In 2 and ½ months after the admission the patient was discharged from the hospital for ambulatory treatment. During the control examination in the clinic after 9 months, including echography, and scitigraphy of the liver, it was determined that the affected area reduced by one fourth, to three fourths of its original size, and fibroid tissue constituted about 40 percent of the remaining under volume. The patient had no complaints.

EXAMPLE 3

Female Patient C., born in 1931, medical history No. 2130, was admitted to the Institute's clinic with a diagnosis: A cavernous hemangioma of the liver's right lobe. The tumor was detected in another medical institution during a cholecystectomy due to chronic calculous cholecystitis. The patient was disturbed by dull pains and heavy feeling in the right subcostal. The liver echography confirmed a cavernous hemangioma of the liver's right lobe 11-8-7 cm in size in segments 5, 6, and 7. Indirect angiohepatoscintigraphy with pertechnetate technetium showed the enlargement of the arterial component in the tumor's blood circulation. Due to the hemangioma's large size, its close location to the portal vein and the results of the indirect angiohepatoscintigraphy, it was decided to perform an intravascular intrusion. The clinical blood tests showed permanent thrombocitopenia (from $102 \times 10^9/1$ to $133 \times 10^9/1$). The reports of the blood coagulation showed an increase of plasma reacacification time up to 183 seconds.

On the 20th day after admission of the patient, a puncture under local anesthesia by the novocaine solution with additional neuroleptanalgesia of the right femoral artery was done after Seldinger, with selective catheterization of the right kidney artery leading to the hemangioma. Through the catheter, a metal spiral of the Gianturko type was introduced into the vessel until the reduction of the arterial blood flow was achieved. Its level was controlled by X-rays using contrast substance.

During 7 days after the treatment, the patient had dull pains in the liver area. Her temperature increased to 37.8° C. The received antibiotics and analgetics. In 16 days after the intravascular intrusion, a skin-penetrating, liver-penetrating aimed puncture of the hemangioma was done under local anesthesia and under echographic control with an introduction of 20 cm³ of ferromagnetic water suspension, the proportion of the solid and liquid phases being 1:5. The chosen calculated preparation volume made up to 4 percent of the tumor's volume. At the same time, a source of a permanent magnetic field was placed over the liver, its tension at the place of the preparation introduction being 0.6 Tesla. The source of the eternal magnetic field was held over the liver for 10 minutes. During the procedure, and for the following 2 days, the patient felt moderate pain in the liver area, weakness, and loss of appetite. Her temperature was normal. Clinical biochemical reports, including the serum iron level was the same as it was previously. For 5 days the patient received antibiotics. In 6 days after the ferromagnetic embolization she was treated with local hyperthermia with electromagnetic radiation of UHF frequencies. The power was 15 watts, and the duration was 45 minutes. During, and after the procedure the patient had no complaints. Her hemodynamic reports and her condition remained unchanged. The next day during a control X-ray examination of the abdominal cavity, a steady and compact location of the preparation of the hemangioma was determined. She was discharged on the same day in satisfactory condition under the observation of the local physician. In 2 months after the treatment, the control ultrasonic examination showed that the hemangioma was reduced by one fourth of its original size, to three fourths of its original size, and fibroid tissue filling 40 percent of its volume. The patient feels well. It is planned to continue the hemangioma treatment by the above mentioned method.

OTHER ADVANTAGES OF THE INVENTION

One advantage of the present invention is the creation of a compact magnetic system in the hemangioma area together with the reduction of the blood flow. This method, demonstrated here for the first time, provides for the hemangioma's complete local thrombosis due to the influence on the arterial as well as the venous components of the blood circulation.

Other advantages of the use of this method are that it prevents the development of a wide tumor necrosis, and it reduces general intoxication and the possibility of the development of septic complications or hepatic insufficiency. These advantages broaden the possibilities of its application, including patients in the most grave conditions.

REFERENCES

1. Gorvin-Yehudain J., Moscona A. R., Calderon N., Hirshowitz B.; "Treatment of Hemangiomas by Sclerosing Agents: An Experimental and Clinic Study"; *Ann. of Plastic Surgery*, Vol. 18, No. 6, 1987. pp. 464–469.
2. Drudarski B., Radojnovie, Perovic M., Nadj G., Dinamicka; "Kompjuterovana tomografija kavernosnoy hemahgioma jetre"; *Radiol. ingosl.*, Vol. 22, No. 4, 1988, pp. 568-370.
3. Sinanan M. N., Marchiro; T.; "Management of cavernous hemangioma of the liver"; *Am. Journal of Surgery*, Vol. 157, No. 5, 1989; pp. 519-522.
4. Kuzin M. I., Volynskiy Y. D., Guseynov E. K.; "The place of X-ray endovascular intrusions in the surgery of focally affected liver"; *Surgery*, Vol. 14, 1989, p. 146.
5. Bornman P. C., Terblaucnne J., Blumgart R. L., Jones E. P. H., Kalvaria I.; "Giant hepatic hemangiomas: Diagnostic and therapeutic dilemmas", *Surgery*, Vol. 101, Vol. 4, 1987, pp,. 445-449.
6. Anderenson R., Bengmark S.; "Surgical treatment of cavernous hemangioma of the liver."; *Acta clin. Scand.*, Vol. 154, No. 10, 1988, pp. 577-579.
7. Rohner A.; *Schweiz. Med. Wschn.*, Bd. 116, 31/32, 1986, S 1044–1050.
8. Nagao T., Jnoue S., Mizuta T. et. al.; *Ann. Surg.* Vol. 202, 1985, pp. 42-49.
9. Nishida O., Satoh N., Alam S., Uchino J.; "The effect of hepatic artery ligation for irresectable cavernous hemangioma of the liver."; *Amer. Surg.*, Vol. 54, No. 8, 1988, pp. 483-486.

10. Rabkin I. H., Matveyev A. L., Gotman L. N.; "X-ray endovascular surgery."; *M. Medicine*, 1987, p. 400-401.

11. Reading N. G., Forbes A., Nunnerly H. B., Williams R.: "Hepatic hemangioma a critical review of diagnosis and management."; *Quart. J. Med.*, Vol. 67, No. 253, 1988, pp. 431-445.

12. Falappa P., Patane D., Cotroneo A. R. et. al.; "II ruolo della radiologia interventiva nei tumoriefactici benigni"; *Acta Med. Romana*, Vol. 24, No. 1, 1986, pp. 63-73.

What is claimed is:

1. A method of hemangioma treatment comprising:
   selectively catheterizing a supplying artery of a hemangioma tissue site with a metal spiral Gianturko type catheter;
   acquiring an ultrasonic image of the hemangioma tissue site via an ultrasonic imaging device;
   introducing a hard ferromagnetic substance into the hemangioma tissue site via said catheter until said substance fills not more than thirty percent of the volume of the hemangioma tissue site, on the basis of said ultrasonic image;
   applying an electromagnetic field of UHF frequencies to the hemangioma tissue site for a duration of 10 minutes or more.

2. A method according to claim 1, wherein said hard ferromagnetic substance is barium hexaferrite used in the form of a suspension in 0.9 percent sodium chloride solution, the proportion of the solid barium hexaferrite and liquid sodium chloride solution being in the range of 1:5 to 1:10.

3. A method according to claim 1, wherein said step of applying an electromagnetic field is performed once or repeatedly until a full hemangioma thrombosis is achieved, said thrombosis thereafter producing a fibrosis of the hemangioma tissue site.

4. A method of hemangioma treatment comprising:
   selectively catheterizing a supplying artery of a hemangioma tissue site with a metal spiral Gianturko type catheter;
   acquiring an ultrasonic image of the hemangioma tissue site via an ultrasonic imaging device;
   introducing a hard ferromagnetic substance into the hemangioma tissue site via said catheter until said substance fills not more than thirty percent of the volume of the hemangioma tissue site, on the basis of said ultrasonic image;
   applying ultrasonic energy to the hemangioma tissue site for a duration of 10 minutes or more.

5. A method according to claim 4, wherein said step of applying ultrasonic energy is performed once or repeatedly until a full hemangioma thrombosis is achieved, said thrombosis thereafter producing a fibrosis of the hemangioma tissue site.

6. A method according to claim 4, wherein said hard ferromagnetic substance is barium hexaferrite used in the form of a suspension in 0.9 percent sodium chloride solution, the proportion of the solid barium hexaferrite and liquid sodium chloride solution being in the range of 1:5 to 1:10.

* * * * *